US006579715B1

(12) United States Patent
Friedrich et al.

(10) Patent No.: US 6,579,715 B1
(45) Date of Patent: Jun. 17, 2003

(54) MAMMALIAN CORTEXIN-LIKE PROTEINS AND POLYNUCLEOTIDES ENCODING THE SAME

(75) Inventors: Glenn Friedrich, Houston, TX (US); Michael C. Nehls, Stockdorf (DE)

(73) Assignee: Lexicon Genetics Incorporated, The Woodlands, TX (US)

(*) Notice: Subject to any disclaimer, the term of this patent is extended or adjusted under 35 U.S.C. 154(b) by 0 days.

(21) Appl. No.: 09/484,906

(22) Filed: Jan. 18, 2000

Related U.S. Application Data

(60) Provisional application No. 60/116,310, filed on Jan. 19, 1999.

(51) Int. Cl.[7] .................. C12N 15/63; C07H 21/04; C07K 5/00; A61K 48/00
(52) U.S. Cl. .................. 435/320.1; 536/23.1; 536/23.5; 536/24.31; 530/300; 530/326; 530/327; 514/44; 930/10
(58) Field of Search .................. 435/320.1; 536/23.1, 536/23.5, 24.31; 530/300, 326, 327; 514/44; 930/10

(56) References Cited

U.S. PATENT DOCUMENTS

| | | | |
|---|---|---|---|
| 4,376,110 A | 3/1983 | David et al. | |
| 4,683,202 A | 7/1987 | Mullis | |
| 4,873,191 A | 10/1989 | Wagner et al. | |
| 4,946,778 A | 8/1990 | Ladner et al. | |
| 5,075,217 A | 12/1991 | Weber | |
| 5,364,759 A | 11/1994 | Caskey et al. | |
| 5,837,458 A | 11/1998 | Minshull et al. | |

FOREIGN PATENT DOCUMENTS

| | | |
|---|---|---|
| WO | WO98/37175 | 8/1998 |
| WO | WO98/40483 | 9/1998 |
| WO | WO98/41628 | 9/1998 |
| WO | WO 99/06551 | 2/1999 |

OTHER PUBLICATIONS

Smith et al. The challenges of genome sequence annotation or "The devil is in the details", Nov. 1997, vol. 15, p. 1222–1223.*
Doerks et al. Protein Annotation: detective work for function prediction, Jun. 1998, vol. 14, No. 6, p248–250.*
Khavinson et al. The effect of brain peptides on nerve tissue cells in vitro, Tsitologiia, 1997, vol. 39, No. 7, pp. 571–576. (abstract) Medline [online]. Bethesda, MD, USA: United States National Library of Medicine retrieved on Oct. 21, 2002.*
Khavinson et al. Cortexin effectiveness in circulatory encephalopathy, Klin Med (Mosk), 1999, vol. 77, No. 4, pp. 42–45. (abstract) Medline [online]. Bethesda, MD, USA: United States National Library of Medicine retrieved on Oct. 21, 2002.*
Bonaldo et al., Genome Research (1996) 6(9):791–806.*
Bird et al, 1988, "Single–Chain Antigen–Binding Proteins", Science 242:423–426.
Bitter et al, 1987, "Expression and Secretion Vectors for Yeast", Methods in Enzymology 153:516–544.
Butler, J.E., 1981, "The Amplified ELISA: Principles of and Applications for the Comparative Quantitation of Class and Subclass Antibodies and the Distribution of Antibodies and Antigens in Biochemical Separates", Meth. Enzymol. 73:482–523.
Colbere–Garapin et al, 1981, "A New Dominant Hybrid Selective Marker for Higher Eukaryotic Cells", J. Mol. Biol. 150:1–14.
Cote et al, 1983, "Generation of human monoclonal antibodies reactive with cellular antigens", Proc. Natl. Acad. Sci. USA 80:2026–2030.
Gautier et al, 1987, "α–DNA IV:α–anomeric and β–anomeric tetrahymidylates covalently linked to intercalating oxazolopyridocarbazole. Synthesis, physiochemical properties and poly (rA) binding", Nucleic Acids Research 15(16):6625–6641.
Gordon, 1989, "Transgenic Animals", Intl. Rev. Cytol. 115:171–229.
Greenspan et al, 1993, "Idiotypes: structure and immunogenicity", FASEB Journal 7:437–444.
Gu et al, 1994, "Deletion of a DNA Polymerase β Gene Segment in T Cells Using Cell Type–Specific Gene Targeting", Science 265:103–106.
Huse et al, 1989, "Generation of a Large Combinatorial Library of the Immunoglobulin Repertoire in Phage Lambda", Science 246:1275–1281.
Huston et al, 1988, "Protein engineering of antibody binding sites: Recovery of specific activity in an anti–digoxin single–chain Fv analogue produced in *Escherichia coli*", Proc. Natl. Acad. Sci. USA 85:5879–5883.
Inoue et al, 1987, "Sequence–dependent hydrolysis of RNA using modified oligonucleotide splints and R Nase H", FEBS Letters 215(2):327–330.
Inoue et al, 1987, "Synthesis and hybridization studies on two complementary nona(2'–O–methyl)ribonucleotides", Nucleic Acids Research 15(15):6131–6149.
Inouye & Inouye, 1985, "Up–promoter mutations in the lpp gene of *Escherichia coli*", Nucleic Acids Research 13(9):3101–3110.
Janknecht et al, 1991, "Rapid and efficient purification of native histidine–tagged protein expressed by recombinant vaccinia virus", Proc. Natl. Acad. Sci. USA 88:8972–8976.
Lakso et al, 1992, "Targeted oncogene activation by site–specific recombination in transgenic mice", Proc. Natl. Acad. Sci. USA 89:6232–6236.
Lavitrano et al, 1989, "Sperm Cells as Vectors for Introducing Foreign DNA into Eggs: Genetic Transformation of Mice", Cell 57:717–723.

(List continued on next page.)

*Primary Examiner*—Christopher S. F. Low
*Assistant Examiner*—Holly Schnizer

(57) ABSTRACT

The human and murine homologues of a novel cortexin-like protein are described.

6 Claims, No Drawings

OTHER PUBLICATIONS

Lo, 1983, "Transformation by Iontophoretic Microinjection of DNA: Multiple Integrations without Tandem Insertions", Mol. & Cell. Biology 3(10):1803–1814.

Logan et al, 1984, "Adenovirus tripartite leader sequence enhances translation of mRNAs late after infection", Proc. Natl. Acad. Sci. USA 81:3655–3659.

Lowy et al, 1980, "Isolation of Transforming DNA: Cloning the Hamster aprt Gene", Cell 22:817–823.

Miyajima et al, 1986, "Expression of murine and human granulocyte–macrophase colony–stimulating factors in S. cerevisiae: mutagenesis of the potential glycosylation sites", EMBO J. 5(6):1193–1197.

Morrison et al, 1984, "Chimeric human antibody molecules: Mouse antigen–binding domains with human constant region domains", Proc. Natl. Acad. Sci. USA 81:6851–6855.

Mulligan & Berg, 1981, "Selection for animal cells that express the Escherichia coli gene coding for xanthine–guanine phosphoribosyltransferase", Proc. Natl. Acad. Sci. USA 78(4):2072–2076.

Neuberger et al, 1984, "Recombinant antibodies possessing novel effector functions", Nature 312:604–608.

Nisonoff, 1991, "Idiotypes: Concepts and Applications", J. of Immunology 147:2429–2438.

O'Hare et al, 1981, "Transformation of mouse fibroblasts to methotrexate resistance by a recombinant plasmid expressing a prokaryotic dihydrofolate reductase", Proc. Natl. Acad. Sci. USA 78(3):1527–1531.

Ruther et al, 1983, "Easy identification of cDNA clones", EMBO Journal 2(10):1791–1794.

Santerre et al, 1984, "Expression of prokaryotic genes for hygromycin B and G418 resistance as dominant–selection markers in mouse L cells", Gene 30:147–156.

Sarin et al, 1988, "Inhibition of acquired immunodeficiency syndrome virus by oligodeoxynucleoside methylphosphonates", Proc. Natl. Acad. Sci. USA 85:7448–7451.

Smith et al, 1983, "Molecular Engineering of the Autographa californica Nuclear Polyhedrosis Virus Genome: Deletion Mutations within the Polyhedrin Gene", J. Virol. 46(2):584–593.

Stein et al, 1988, "Physiochemical properties of phosphorothioate oligodeoxynucleotides", Nucleic Acids Research 16(8):3209–3221.

Szybalska & Szybalski, 1962, "Genetics of Human Cell Lines, IV. DNA–Mediated Heritable Transformation of a Biochemical Trait", Proc. Natl. Acad. Sci. USA 48:2026.

Takeda et al, 1985, "Construction of chimaeric processed immunoglobulin genes containing mouse variable and human constant region sequences", Nature 314:452–454.

Thompson et al, 1989, "Germ Line Transmission and Expression of a Corrected HPRT Gene Produced by Gene Targeting in Embryonic Stem Cells", Cell 56:313–321.

Van Der Putten et al, 1985, "Efficient insertion of genes into the mouse germ line via retroviral vectors", Proc. Natl. Acad. Sci. USA 82:6148–6152.

Van Heeke & Schuster, 1989, "Expression of Human Asparagine Synthetase in Escherichia coli", J. Biol. Chem. 264(10):5503–5509.

Voller, A. et al, 1978, "Enzyme immunoassays with special reference to ELISA techniques", J. Clin. Pathol. 31:507–520.

Ward et al, 1989, "Binding activities of a repertoire of single immunoglobulin variable domains secreted from Escherichia coli", Nature 341:544–546.

Wigler et al, 1977, "Transfer of Purified Herpes Virus Thymidine Kinase Gene to Cultured Mouse Cells", Cell 11:223–232.

Wigler et al, 1980, "Transformation of mammalian cells with an amplifiable dominant–acting gene", Proc. Natl. Acad. Sci. USA 77(6):3567–3570.

Coulter et al, 1993, "Identification of Cortexin: A Novel, Neuron–Specific, 82–Residue Membrane Protein Enriched in Rodent Cerebral Cortex", Journal of Neurochemistry 61(2):756–759.

NCI–CGAP, 1999, "National Cancer Institute, cancer genome anatomy project (CGAP), Tumor gene index", EMBL Database Entry AI657089. XP002140014 * 86M 7% Identity with sequence ID no. 1 in 249 bp overlap and 99, 6% identity in 246 bp overlap with sequence ID no. 3. reverse orientation * & Unpublished.

NCI–CGAP, 1999, "National Cancer Institute, cancer genome anatomy project (CGAP), Tumor gene index", EMBL Database Entry AI867720, XP002140015 * 99,2% Identity IN 247 bp overlap with sequence ID. 3 AND 86,4% identity in 250 bp overlap with sequence ID no. 1 * & Unpublished.

* cited by examiner

SEQUENCE LISTING

<160> NUMBER OF SEQ ID NOS: 4

<210> SEQ ID NO 1
<211> LENGTH: 249
<212> TYPE: DNA
<213> ORGANISM: Mus musculus

<400> SEQUENCE: 1

```
atgatgagta gcacctactg tggcaattct tcagcaaaga tgagtgtcca cgaagtctct      60
gaatcctccc tgtctctgga gcaaaagacc ggctttgcct ttgtgggcat cttgtgcatt     120
ttcttgggac ttctcattat cagatgcttc aagattctgt tagacccata tagtagcatg     180
ccctcttcta catgggaaga tgaagttgaa gagtttgata aggggacctt tgagtatgca     240
cttgcctga                                                             249
```

<210> SEQ ID NO 2
<211> LENGTH: 82
<212> TYPE: PRT
<213> ORGANISM: Mus musculus

<400> SEQUENCE: 2

```
Met Met Ser Ser Thr Tyr Cys Gly Asn Ser Ser Ala Lys Met Ser Val
 1               5                  10                  15

His Glu Val Ser Glu Ser Ser Leu Ser Leu Glu Gln Lys Thr Gly Phe
            20                  25                  30

Ala Phe Val Gly Ile Leu Cys Ile Phe Leu Gly Leu Leu Ile Ile Arg
        35                  40                  45

Cys Phe Lys Ile Leu Leu Asp Pro Tyr Ser Ser Met Pro Ser Ser Thr
    50                  55                  60

Trp Glu Asp Glu Val Glu Glu Phe Asp Lys Gly Thr Phe Glu Tyr Ala
65                  70                  75                  80

Leu Ala
```

<210> SEQ ID NO 3
<211> LENGTH: 246
<212> TYPE: DNA
<213> ORGANISM: Homo sapiens

<400> SEQUENCE: 3

```
atgagtagta cctactgtgg caactcttca gctaagatga gtgtcaacga agtatcagct      60
ttctcattga ctctggagca aaaaactggc tttgcttttg ttgggatttt gtgtatcttc     120
ttgggacttc ttattatccg atgcttcaaa atcctgctag acccatatag tagcatgcct     180
tcctttacat gggaagatga agttgaagag tttgataaag gacatttga atatgcactc     240 gcgtga                                                                246
```

<210> SEQ ID NO 4
<211> LENGTH: 81
<212> TYPE: PRT
<213> ORGANISM: Homo sapiens

<400> SEQUENCE: 4

```
Met Ser Ser Thr Tyr Cys Gly Asn Ser Ser Ala Lys Met Ser Val Asn
 1               5                  10                  15

Glu Val Ser Ala Phe Ser Leu Thr Leu Glu Gln Lys Thr Gly Phe Ala
            20                  25                  30
```

-continued

```
Phe Val Gly Ile Leu Cys Ile Phe Leu Gly Leu Leu Ile Ile Arg Cys
        35              40              45

Phe Lys Ile Leu Leu Asp Pro Tyr Ser Ser Met Pro Ser Phe Thr Trp
        50              55              60

Glu Asp Glu Val Glu Glu Phe Asp Lys Gly Thr Phe Glu Tyr Ala Leu
65              70              75              80

Ala
```

MAMMALIAN CORTEXIN-LIKE PROTEINS AND POLYNUCLEOTIDES ENCODING THE SAME

1. INTRODUCTION

The present application claims priority to U.S. application Ser. No. 60/116,310 which was filed Jan. 19, 1999 and is incorporated herein in its entirety. The present invention relates to the discovery, identification, and characterization of novel mammalian polynucleotide sequences and the novel polypeptides encoded thereby. The invention encompasses the described human polynucleotides, and a novel murine homolog thereof, host cell expression systems, the encoded human and murine proteins or polypeptides, and fusion proteins and peptides derived therefrom, antibodies to the encoded proteins or peptides, and genetically engineered animals that lack the disclosed gene, over express the disclosed gene, as well as antagonists and agonists of the proteins, along with other compounds that modulate the expression or activity of the protein encoded by the disclosed gene that can be used for diagnosis, drug screening, clinical trial monitoring, the treatment of physiological or behavioral disorders, or to otherwise improve quality of life.

2. BACKGROUND OF THE INVENTION

Proteins are the major structural and regulatory components of life. In particular, secreted proteins, or circulating fragments or portions of other proteins, can interact with protein receptors to regulate and maintain a wide variety of biological and physiological processes. Often, such processes are mediated by protein ligands that interact with corresponding membrane receptor proteins that activate signal transduction and other pathways that control cell physiology, chemical release and communication, and gene expression. As such, protein/receptor interactions constitute preferred targets for drug intervention and for the design of therapeutic agents.

3. SUMMARY OF THE INVENTION

The present invention relates to the discovery, identification, and characterization of nucleotides that encode two novel mammalian proteins, and the corresponding amino acid sequences encoded by the disclosed nucleotide sequences. Both genes share limited similarity with the rat cortexin protein and are thus referred to as cortexin-like proteins (CLPs). The novel human protein described for the first time herein is referred to as human cortexin-like protein (HCLP). The novel human nucleic acid sequence described herein, encodes a protein of 81 amino acids in length (SEQ ID NO: 4), and the gene encoding the novel murine cortexin-like protein (MCLP) encodes a sequence of 82 amino acids (SEQ ID NO: 2). The described CLPs may lack one or more amino acids (cleaved from either end, or, more typically, the N-terminus, e.g., at a signal sequence or other proteolytic cleavage/processing site) when the CLPs are present in the cell membrane.

Given that the murine homolog of the described HCL has been identified, "knockout" ES cells have been produced using gene trap technology essentially as described in U.S. application Ser. No. 08/942,806, filed Oct. 2, 1997, herein incorporated by reference. Conventional methods (see, for example, PCT Applic. No. PCT/US98/03243, filed Feb. 20, 1998, herein incorporated by reference) can also be used to generate mutant animals by gene targeting. Accordingly, an additional aspect of the present invention includes knockout cells and animals having genetically engineered mutations in gene encoding the presently described proteins.

The invention encompasses the nucleotides presented in the Sequence Listing, host cells expressing such nucleotides, and the expression products of such nucleotides, and: (a) nucleotides that encode mammalian homologs of the described gene products; (b) nucleotides that encode one or more portions of the described genes that correspond to functional domains, and the polypeptide products specified by such nucleotide sequences, including but not limited to the novel regions of any active domain(s); (c) isolated nucleotides that encode mutant versions, engineered or naturally occurring, of the described proteins in which all or a part of at least one domain is deleted or altered, and the polypeptide products specified by such nucleotide sequences, including but not limited to soluble proteins and peptides in which all or a portion of the signal sequence in deleted; (d) nucleotides that encode chimeric fusion proteins containing all or a portion of a coding region of the disclosed genes, or one of its domains (e.g., a receptor/ligand binding domain, accessory protein/self-association domain, etc.) fused to another peptide or polypeptide.

The invention also encompasses agonists and antagonists of the described proteins, including small molecules, large molecules, mutant HCLPs, or portions thereof that compete with native HCLP, and antibodies, as well as nucleotide sequences (e.g., antisense and ribozyme molecules, and gene or regulatory sequence replacement constructs) that can be used to inhibit the expression of the described HCLP and MCLP products, or to enhance the expression of the corresponding genes (e.g., expression constructs that place the described gene under the control of a strong promoter system), and transgenic animals that express a HCLP or MCLP transgene, or "knock-outs" (which can be conditional) that do not express functional MCLP.

Further, the present invention also relates to methods for the use of the described genes and products for the identification of compounds that modulate, i.e., act as agonists or antagonists, of HCLP or MCLP expression and/or HCLP or MCLP activity. Such compounds can be used as therapeutic agents for the treatment of any of a wide variety of symptomatic representations of biological disorders or imbalances.

Additionally contemplated are therapeutic applications of the described HCLP as well as the use of HCLP in the production of a medicament for treatment of encephalopathy, and particularly dyscirculatory encephalopathy.

4. DESCRIPTION OF THE SEQUENCE LISTING AND FIGURES

The Sequence Listing provides the sequences of the described HCLP and MCLP open reading frames (ORFs), and the amino acid sequences encoded thereby.

5. DETAILED DESCRIPTION OF THE INVENTION

The presently described novel gene sequences are exemplary of a novel gene locus that, for the purposes of this disclosure, shall generically be referred to as the cortexin-like protein (CLP) gene. Depending upon the context of the disclosure the term CLP (or as modified by a designation of species, e.g., HCLP or MCLP) may interchangeably be used in conjunction with language denoting the CLP amino acid sequence (of the CLP protein or any portion thereof), or the CLP nucleotide sequence (of a CLP gene or any portion thereof).

The HCLP and MCLP described for the first time herein, are novel proteins that are expressed, inter alia, in brain and testis. The described proteins have structural motifs typical of integral membrane proteins, and are presumed to be such, but CLPs, or proteolytic cleavage products thereof, can also exert biological effect by acting as ligands that interact with cell surface receptors. Because such ligands/secreted proteins are considered to be more likely to effect some biological activity (via their cognate receptors), the genes encoding such proteins (and the proteins encoded thereby as well as the uses and formulations thereof) have been the subjects of intense scientific and commercial scrutiny (see, for example, Applic. Ser. Nos. PCT/US98/04858 (from 60/068,368, 60/057,765, 60/048,970, 60/040,762 and others listed on the face of the application) filed Mar. 12, 1998, Ser. No. 09/040,963, filed Mar. 18, 1998, PCT/US98/05255 (corresponding to Ser. No. 60/041,263), filed Mar. 18, 1998, all of which are herein incorporated by reference in their entirety).

The invention encompasses the use of the described HCLP nucleotides, HCLP (and peptide fragments thereof), as well as antibodies, preferably humanized monoclonal antibodies, or binding fragments, domains, or fusion proteins thereof, or antiidotypic variants derived therefrom, that bind HCLP (which can, for example, also act as HCLP agonists or antagonists), other antagonists that inhibit binding activity or expression, or agonists that activate HCLP receptor activity or increase HCLP expression, in the diagnosis and/or treatment of disease.

In particular, the invention described in the subsections below encompasses HCLP and MCLP polypeptides or peptides corresponding to functional domains of HCLP or MCLP, mutated, truncated or deleted HCLPs or MCLPs (e.g., HCLPs or MCLPs missing one or more functional domains or portions thereof), HCLP or MCLP fusion proteins (e.g., HCLP or MCLP, or a functional domain of HCLP or MCLP, fused to an unrelated protein or peptide such as an immunoglobulin constant region, i.e., IgFc), nucleotide sequences encoding such products, and host cell expression systems that can produce such HCLP or MCLP products.

The invention also encompasses antibodies and anti-idiotypic antibodies (including Fab fragments), antagonists and agonists of HCLP, as well as compounds or nucleotide constructs that inhibit expression of a HCLP or MCLP gene (transcription factor inhibitors, antisense and ribozyme molecules, or gene or regulatory sequence replacement constructs), or promote expression of HCLP or MCLP (e.g., expression constructs in which the HCLP or MCLP coding sequences are operatively associated with expression control elements such as promoters, promoter/enhancers, etc.). The invention also relates to host cells and animals genetically engineered to express HCLP or MCLP (or mutant variants thereof) or to inhibit or "knock-out" expression of an endogenous animal homolog of the HCLP gene.

HCLP or MCLP, or peptides therefrom, HCLP or MCLP fusion proteins, and HCLP or MCLP nucleotide sequences, antibodies, antagonists and agonists can be useful for the detection of mutant variants or inappropriately expressed HCLP or MCLP for the diagnosis of disease. The described proteins or peptides, fusion proteins, nucleotide sequences, host cell expression systems, antibodies, antagonists, agonists and genetically engineered cells and animals can also be used for drug screening (or high throughput screening of combinatorial libraries) to identify candidates effective in the treatment of the symptomatic or phenotypic manifestations of perturbing the normal function of HCLP in the body. The use of engineered host cells and/or animals may offer an advantage in that such systems allow not only for the identification of compounds that mimic the ligand or receptor for a HCLP, but can also identify compounds that trigger MCLP- or HCLP-mediated processes.

Finally, HCLP and MCLP products (especially soluble derivatives such as peptides corresponding to the, and fusion protein products (especially HCLP-Ig fusion proteins, i.e., fusions of a HCLP, or a domain of a HCLP, to an IgFc), antibodies and anti-idiotypic antibodies (including Fab fragments), antagonists or agonists (including compounds that modulate signal transduction which may act on downstream targets in a HCLP-mediated signal transduction pathway) can be used to directly treat diseases or disorders. For example, the administration of an effective amount of soluble HCLP, or a HCLP-IgFc fusion protein or an anti-idiotypic antibody (or its Fab) that mimics the HCLP could activate or neutralize the endogenous HCLP receptor. Nucleotide constructs encoding such HCLP products can be used to genetically engineer host cells to express such products in vivo; these genetically engineered cells function as "bioreactors" in the body delivering a continuous supply of HCLP, a HCLP peptide, or a HCLP fusion protein to the body. Nucleotide constructs encoding functional HCLP, mutant HCLPs, as well as antisense and ribozyme molecules can also be used in "gene therapy" approaches for the modulation of HCLP expression. Thus, the invention also encompasses pharmaceutical formulations and methods for treating biological disorders.

Various aspects of the invention are described in greater detail in the subsections below.

5.1 HCLP and MCLP Polynucleotides

The cDNA sequences (SEQ ID NOS: 1 and 3) and deduced amino acid sequences (SEQ ID NOS: 2, and 4) of the described proteins are presented in the Sequence Listing. The HCLP gene was obtained from human testis and brain cDNA libraries using probes and/or primers generated from gene trapped sequence tags. The MCLP gene was identified as a gene trapped sequence present in the OMNIBANK® library of gene trap mutagenized murine ES cells.

The HCLP gene of the present invention includes: (a) the human DNA sequence presented in the Sequence Listing and additionally contemplates any nucleotide sequence encoding a contiguous and functional HCLP open reading frame (ORF) that hybridizes to a complement of the DNA sequences presented in the Sequence Listing under highly stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encodes a functionally equivalent gene product. Functional equivalents of a NHP include naturally occurring NHPs present in other species and mutant NHPs whether naturally occurring or engineered (by site directed mutagenesis, gene shuffling, directed evolution as described in, for example, U.S. Pat. No. 5,837,458). The invention also includes degenerate nucleic acid variants of the disclosed NHP polynucleotide sequences.

Additionally contemplated are any nucleotide sequences that hybridize to the complement of the DNA sequences that encode and express an amino acid sequence presented in the Sequence Listing under moderately stringent conditions, e.g., washing in 0.2×SSC/0.1% SDS at 42° C. (Ausubel et al., 1989, supra), yet which still encode a functionally equivalent product. Functional equivalents of HCLP or MCLP include naturally occurring homologues present in other species, and mutant variants, whether naturally occurring or engineered. The invention also includes degenerate variants of the disclosed sequences.

The invention also includes nucleic acid molecules, preferably DNA molecules, that hybridize to, and are therefore the complements of, the described nucleotide sequences. Such hybridization conditions may be highly stringent or less highly stringent, as described above. In instances wherein the nucleic acid molecules are deoxyoligonucleotides ("DNA oligos"), such molecules (and particularly about 16 to about 100 base long, about 20 to about 80, or about 34 to about 45 base long, or any variation or combination of sizes represented therein incorporating a contiguous region of sequence first disclosed in the present Sequence Listing, can be used in conjunction with the polymerase chain reaction (PCR) to screen libraries, isolate clones, and prepare cloning and sequencing templates, etc.

Alternatively, such NHP oligonucleotides can be used as hybridization probes for screening libraries, and assessing gene expression patterns (particularly using a micro array or high-throughput "chip" format). Additionally, a series of the described NHP oligonucleotide sequences, or the complements thereof, can be used to represent all or a portion of the described NHP sequences. The oligonucleotides, typically between about 16 to about 40 (or any whole number within the stated range) nucleotides in length may partially overlap each other and/or the NHP sequence may be represented using oligonucleotides that do not overlap. Accordingly, the described NHP polynucleotide sequences shall typically comprise at least about two or three distinct oligonucleotide sequences of at least about 18, and preferably about 25, nucleotides in length that are each first disclosed in the described Sequence Listing. Such oligonucleotide sequences may begin at any nucleotide present within a sequence in the Sequence Listing and proceed in either a sense (5'-to-3') orientation vis-a-vis the described sequence or in an antisense orientation.

For oligonucleotide probes, highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as HCLP or MCLP gene antisense molecules, useful, for example, in HCLP or MCLP gene regulation (for and/or as antisense primers in amplification reactions of HCLP or MCLP gene nucleic acid sequences). With respect to gene regulation, such techniques can be used to regulate biological functions. Further, such sequences may be used as part of ribozyme and/or triple helix sequences, also useful for HCLP or MCLP gene regulation.

Additionally, the antisense oligonucleotides may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330).

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual (and periodic updates thereof), Cold Springs Harbor Press, N.Y.; and Ausubel et al., 1989, Current Protocols in Molecular Biology, Green Publishing Associates and Wiley Interscience, N.Y.

Alternatively, suitably labeled HCLP nucleotide probes may be used to screen a human genomic library using appropriately stringent conditions or by PCR. The identification and characterization of human genomic clones is helpful for identifying polymorphisms, determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

Further, a HCLP or MCLP gene homolog may be isolated from nucleic acid of the organism of interest by performing PCR using two degenerate oligonucleotide primer pools designed on the basis of amino acid sequences within the presently described products. The template for the reaction may be total RNA, mRNA, and/or cDNA obtained by reverse transcription of mRNA prepared from, for example, human or non-human cell lines or tissue, such as brain, known or suspected to express a HCLP or MCLP gene/allele.

The PCR product may be subcloned and sequenced to ensure that the amplified sequences represent the sequence of the desired gene. The PCR fragment may then be used to isolate a full length cDNA clone by a variety of methods. For example, the amplified fragment may be labeled and used to screen a cDNA library, such as a bacteriophage cDNA library. Alternatively, the labeled fragment may be used to isolate genomic clones via the screening of a genomic library.

PCR technology may also be utilized to isolate full length cDNA sequences of homologs of the described genes. For example, RNA may be isolated, following standard procedures, from an appropriate cellular or tissue source (i.e., one known, or suspected, to express a CLP gene, such as, for example, brain tissue). A reverse transcription (RT) reaction may be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment may easily be isolated. For a review of cloning strategies which may be used, see e.g., Sambrook et al., 1989, supra.

A cDNA of a mutant HCLP or MCLP gene may be isolated, for example, by using PCR. In this case, the first cDNA strand may be synthesized by hybridizing an oligo-dT oligonucleotide to mRNA isolated from tissue known or suspected to be expressed in an individual putatively carrying a mutant HCLP, for example, allele, and by extending the new strand with reverse transcriptase. The second strand of the cDNA is then synthesized using an oligonucleotide that hybridizes specifically to the 5' end of the normal gene. Using these two primers, the product is then amplified via PCR, optionally cloned into a suitable vector, and subjected to DNA sequence analysis through methods well known to those of skill in the art. By comparing the DNA sequence of the mutant allele to that of the normal allele, the mutation(s) responsible for the loss or alteration of function of the mutant gene product can be ascertained.

Alternatively, a genomic library can be constructed using DNA obtained from an individual suspected of or known to carry the mutant allele, or a cDNA library can be constructed using RNA from a tissue known, or suspected, to express the mutant allele. A normal HCLP or MCLP gene, or any suitable fragment thereof, can then be labeled and used as a probe to identify the corresponding mutant allele in such libraries. Clones containing the mutant gene sequences can then be purified and subjected to sequence analysis using established methods.

Additionally, an expression library can be constructed utilizing cDNA synthesized from, for example, RNA isolated from a tissue known, or suspected, to express a mutant CLP allele in an individual suspected of or known to carry such a mutant allele. In this manner, gene products made by the putatively mutant tissue may be expressed and screened using standard antibody screening techniques in conjunction with antibodies raised against the normal CLP product, as described, below, in Section 5.3. (For screening techniques, see, for example, Harlow, E. and Lane, eds., 1988, "Antibodies: A Laboratory Manual", Cold Spring Harbor Press, Cold Spring Harbor.)

Additionally, screening can be accomplished by screening with labeled CLP fusion proteins, such as, for example, AP-CLP or CLP-AP fusion proteins. In cases where a CLP mutation results in an expressed gene product with altered function (e.g., as a result of a missense or a frameshift mutation), a polyclonal set of antibodies to CLP are likely to cross-react with the mutant CLP gene product. Library clones detected via their reaction with such labeled antibodies can be purified and subjected to sequence analysis according to methods well known to those of skill in the art.

The invention also encompasses nucleotide sequences that encode mutant CLPs, and particularly HCLPs, peptide fragments of the CLPs, truncated CLPs, and CLP fusion proteins. These include, but are not limited to nucleotide sequences encoding mutant CLPs described in section 5.2 infra; polypeptides or peptides corresponding to one or more domains of the CLP or portions of these domains; truncated CLPs in which one or more of the domains is deleted, or a truncated nonfunctional CLP. Nucleotides encoding fusion proteins may include, but are not limited to, full length CLP sequences, truncated CLPs, or nucleotides encoding peptide fragments of a CLP fused to an unrelated protein or peptide, such as for example, a CLP domain fused to an Ig Fc domain which increases the stability and half life of the resulting fusion protein (e.g., CLP-Ig) in the bloodstream; or an enzyme such as a fluorescent protein or a luminescent protein which can be used as a marker.

The invention also encompasses (a) DNA vectors that contain any of the foregoing HCLP or MCLP coding sequences and/or their complements (i.e., antisense); (b) DNA expression vectors that contain any of the foregoing HCLP or MCLP coding sequences operatively associated with a regulatory element that directs the expression of the coding sequences; (c) genetically engineered host cells that contain any of the foregoing HCLP or MCLP coding sequences operatively associated with a regulatory element that directs the expression of the coding sequences in the host cell; and (d) genetically engineered host cells that express an endogenous CLP gene under the control of an exogenously introduced regulatory element (i.e., gene activation). As used herein, regulatory elements include but are not limited to inducible and non-inducible promoters, enhancers, operators and other elements known to those skilled in the art that drive and regulate expression. Such regulatory elements include but are not limited to the cytomegalovirus hCMV immediate early gene, egulatable, viral (particularly retroviral LTR promoters) the arly or late promoters of SV40 adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

5.2 CLP Proteins and Polypeptides

CLPs, polypeptides, peptide fragments, mutated, truncated, or deleted forms of the CLPs, and/or CLP fusion proteins can be prepared for a variety of uses, including but not limited to the generation of antibodies, as reagents in diagnostic assays, the identification of other cellular gene products related to a CLP, as reagents in assays for screening for compounds that can be as pharmaceutical reagents useful in the therapeutic treatment of mental, biological, or medical disorders and disease.

The Sequence Listing discloses the amino acid sequences encoded by the described CLP genes. Both the HCLP and MCLP genes have initiator methionines in DNA sequence contexts consistent with translation initiation sites.

The HCLP and MCLP sequences of the invention include the nucleotide amino acid sequences presented in the Sequence Listing as well as analogues and derivatives thereof. Further, corresponding CLP homologues from other species are encompassed by the invention. In fact, any CLP protein encoded by a naturally occurring animal, and preferably mammalian, gene that specifically hybridizes to either of the disclosed CLP nucleotide sequences described in Section 5.1, above, are within the scope of the invention, as are any novel polynucleotide sequences encoding all or any novel portion of an amino acid sequence presented in the Sequence Listing. The degenerate nature of the genetic code is well known, and, accordingly, each amino acid presented in the Sequence Listing, is generically representative of the well known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, J. Darnell et al. eds., Scientific American Books, New York, N.Y., herein incorporated by reference) are generically representative of all the various permutations and combinations of nucleic acid sequences that can encode such amino acid sequences.

The invention also encompasses proteins that are functionally equivalent to the CLPs encoded by the nucleotide sequences described in Section 5.1, as judged by any of a number of criteria, including, but not limited to, the ability to bind a HCLP or MCLP ligand or receptor, the ability to effect an identical or complementary signal transduction, a change in cellular metabolism (e.g., ion flux, tyrosine phosphorylation, etc.), or change in phenotype when the CLP equivalent is similarly expressed or mutated in an appropriate cell type (such as the amelioration, prevention or delay of a biochemical, biophysical, or overt phenotype. Such functionally equivalent CLP proteins include, but are not limited to, additions or substitutions of amino acid residues within the amino acid sequence encoded by the CLP nucleotide sequences described above, in Section 5.1, but which result in a silent change, thus producing a functionally equivalent gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

While random mutations can be made to CLP DNA (using random mutagenesis techniques well known to those skilled in the art) and the resulting mutant CLPs tested for activity, site-directed mutations of the CLP coding sequence can be engineered (using site-directed mutagenesis techniques well known to those skilled in the art) to generate mutant CLPs with increased function, e.g., higher receptor binding affinity, decreased function, and/or increased physiological half-life, and increased signal transduction triggering. One starting point for such analysis is by aligning the disclosed human sequences with corresponding gene/protein sequences from, for example, other mammals in order to identify amino acid sequence motifs that are conserved between different species. Non-conservative changes can be engineered at variable positions to alter function, signal transduction capability, or both. Alternatively, where alteration of function is desired, deletion or non-conservative alterations of the conserved regions (i.e., identical amino acids) can be engineered. For example, deletion or non-conservative alterations (substitutions or insertions) of the various conserved transmembrane domains.

Other mutations to CLP coding sequences can be made to generate CLPs that are better suited for expression, scale up, etc. in the host cells chosen. For example, cysteine residues can be deleted or substituted with another amino acid in order to eliminate disulfide bridges; N-linked glycosylation sites can be altered or eliminated to achieve, for example, expression of a homogeneous product that is more easily recovered and purified from yeast hosts which are known to hyperglycosylate-linked sites. To this end, a variety of amino acid substitutions at one or both of the first or third amino acid positions of any one or more of the glycosylation recognition sequences which occur in the extracellular domain (ECD—N-X-S or N-X-T), and/or an amino acid deletion at the second position of any one or more such recognition sequences in the ECD will prevent glycosylation of the CLP at the modified tripeptide sequence. (See, e.g., Miyajima et al., 1986, EMBO J. 5(6):1193–1197).

Peptides corresponding to one or more domains of a CLP, truncated or deleted CLPs, as well as fusion proteins in which a full length CLP, a CLP, peptide, or truncated CLP is fused to an unrelated protein, are also within the scope of the invention and can be designed on the basis of the presently disclosed HCLP gene or MCLP gene nucleotide and HCLP and MCLP amino acid sequences. Such fusion proteins include, but are not limited to, IgFc fusions which stabilize the HCLP protein or peptide, for example, and prolong half-life in vivo; or fusions to any amino acid sequence that allows the fusion protein to be anchored to the cell membrane; or fusions to an enzyme, fluorescent protein, or luminescent protein which provide a marker function.

While the CLPs and peptides can be chemically synthesized (e.g., see Creighton, 1983, Proteins: Structures and Molecular Principles, W. H. Freeman & Co., N.Y.), large polypeptides derived from a CLP and full length CLPs can be advantageously produced by recombinant DNA technology using techniques well known in the art for expressing nucleic acid containing CLP gene sequences and/or coding sequences. Such methods can be used to construct expression vectors containing a CLP nucleotide sequences described in Section 5.1 and appropriate transcriptional and translational control signals. These methods include, for example, in vitro recombinant DNA techniques, synthetic techniques, and in vivo genetic recombination. See, for example, the techniques described in Sambrook et al., 1989, supra, and Ausubel et al., 1989, supra. Alternatively, RNA corresponding to all or a portion of a transcript encoded by a CLP nucleotide sequence may be chemically synthesized using, for example, synthesizers. See, for example, the techniques described in "Oligonucleotide Synthesis", 1984, Gait, M. J. ed., IRL Press, Oxford, which is incorporated by reference herein in its entirety.

A variety of host-expression vector systems may be utilized to express the CLP, and particularly HCLP, nucleotide sequences of the invention. Where the CLP peptide or polypeptide is a soluble derivative (e.g., CLP peptides corresponding to an ECD; truncated or deleted CLP in which a transmembrane (TM) domain and/or cytoplasmic domain (CD) has been deleted) the peptide or polypeptide can be recovered from the culture, i.e., from the host cell in cases where the CLP peptide or polypeptide is not secreted, and from the culture media in cases where the CLP peptide or polypeptide is secreted by the cells. However, such expression systems also encompass engineered host cells that express a CLP, or functional equivalent, in situ, i.e., anchored in the cell membrane. Purification or enrichment of CLPs from such expression systems can be accomplished using appropriate detergents and lipid micelles and methods well known to those skilled in the art. However, such engineered host cells themselves may be used in situations where it is important not only to retain the structural and functional characteristics of the CLP, but to assess biological activity, e.g., in drug screening assays.

The expression systems that may be used for purposes of the invention include but are not limited to microorganisms such as bacteria (e.g., E. coli, B. subtilis) transformed with recombinant bacteriophage DNA, plasmid DNA or cosmid DNA expression vectors containing CLP nucleotide sequences; yeast (e.g., Saccharomyces, Pichia) transformed with recombinant yeast expression vectors containing CLP nucleotide sequences; insect cell systems infected with recombinant virus expression vectors (e.g., baculovirus) containing CLP sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing CLP nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the CLP product being expressed. For example, when a large quantity of such a protein is to be produced for the generation of pharmaceutical compositions of or containing CLP, or CLP peptides, or for raising antibodies to a CLP, vectors that direct the expression of high levels of fusion protein products that are readily purified may be desirable. Such vectors include, but are not limited to, the E. coli expression vector pUR278 (Ruther et al., 1983, EMBO J. 2:1791), in which a CLP coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, Autographa californica nuclear polyhidrosis virus (AcNPV) is used as a vector to express foreign genes. The virus grows in Spodoptera frugiperda cells. A CLP gene coding sequence may be cloned individually into non-essential regions (for example the polyhedrin gene) of the virus and placed under control of an AcNPV promoter (for example the polyhedrin promoter). Successful insertion of CLP gene coding sequence will result in the inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed (e.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the CLP gene nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing a CLP product in infected hosts (e.g., See Logan & Shenk, 1984, Proc. Natl. Acad. Sci. USA 81:3655–3659). Specific initiation signals may also be required for efficient translation of the inserted CLP gene nucleotide sequences. These signals include the ATG initiation codon and adjacent sequences. In cases where an entire CLP gene or cDNA, including its own initiation codon and adjacent sequences, is inserted into the appropriate expression vector, no additional translational control signals may be needed. However, in cases where only a portion of a CLP coding sequence is inserted, exogenous translational control signals, including, perhaps, an ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bittner et al., 1987, Methods in Enzymol. 153:516–544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines which stably express the HCLP and MCLP sequences described above may be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the desired CLP product. Such engineered cell lines may be particularly useful in screening and evaluation of compounds that affect the endogenous activity of the CLP product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk⁻, hgprt⁻ or aprt⁻ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein may be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88: 8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns and histidine-tagged proteins are selectively eluted with imidazole-containing buffers.

CLP, and particularly HCLP, products can also be expressed in transgenic animals. Animals of any species, including, but not limited to, worms, mice, rats, rabbits, guinea pigs, pigs, micro-pigs, birds, goats, and non-human primates, e.g., baboons, monkeys, and chimpanzees may be used to generate CLP transgenic animals.

Any technique known in the art may be used to introduce a CLP transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the CLP transgene in all their cells, as well as animals which carry the transgene in some, but not all their cells, i.e., mosaic animals or somatic cell transgenic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al., 1992, Proc. Natl. Acad. Sci. USA 89:6232–6236. The regulatory sequences required for such a cell-type specific activation will depend upon the particular cell type of interest, and will be apparent to those of skill in the art.

When it is desired that the CLP gene transgene be integrated into the chromosomal site of the endogenous CLP gene, gene targeting is preferred. Briefly, when such a technique is to be utilized, vectors containing some nucleotide sequences homologous to the endogenous CLP gene are designed for the purpose of integrating, via homologous recombination with chromosomal sequences, into and disrupting the function of the nucleotide sequence of the endogenous CLP gene (i.e., "knockout" animals).

The transgene may also be selectively introduced into a particular cell type, thus inactivating the endogenous CLP gene in only that cell type, by following, for example, the teaching of Gu et al., 1994, Science, 265:103–106. The regulatory sequences required for such a cell-type specific inactivation will depend upon the particular cell type of interest, and will be apparent to those of skill in the art.

Once transgenic animals have been generated, the expression of the recombinant CLP gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include but are not limited to Northern blot analysis of tissue samples obtained from the animal, in situ hybridization analysis, and RT-PCR. Samples of CLP gene-expressing tissue, may also be evaluated immunocytochemically using antibodies specific for the CLP transgene product.

Pharmaceutical compositions for use in accordance with the present invention may be formulated in conventional manner using one or more physiologically acceptable carriers or excipients. Thus, the compounds and their physiologically acceptable salts and solvates may be formulated for administration by inhalation or insufflation (either through the mouth or the nose) or oral, buccal, parenteral, intracranial, intrathecal, nasal (including nasal electrophoresis), or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

5.3 Antibodies to CLP Proteins

Antibodies that specifically recognize one or more epitopes of a desired CLP, or epitopes of conserved variants of a CLP, or peptide fragments of a CLP are also encompassed by the invention. Such antibodies include but are not limited to polyclonal antibodies, monoclonal antibodies (mAbs), humanized or chimeric antibodies, single chain antibodies, Fab fragments, F(ab' )$_2$ fragments, fragments produced by a Fab expression library, anti-idiotypic (anti-Id) antibodies, and epitope-binding fragments of any of the above.

The antibodies of the invention may be used, for example, in the detection of HCLP in a biological sample and may, therefore, be utilized as part of a diagnostic or prognostic technique whereby patients may be tested for abnormal amounts of HCLP. Such antibodies may also be utilized in conjunction with, for example, compound screening schemes, or for the evaluation of the effect of test compounds on expression and/or activity of a CLP product. Additionally, such antibodies can be used in conjunction gene therapy to, for example, evaluate the normal and/or engineered CLP-expressing cells prior to their introduction into the patient. Such antibodies may additionally be used as a method for the inhibition of abnormal CLP activity. Thus, such antibodies may, therefore, be utilized as part of treatment methods.

For the production of antibodies, various host animals may be immunized by injection with the CLP, a CLP peptide (e.g., one corresponding the a functional domain of an CLP), truncated CLP polypeptides (CLP in which one or more domains have been deleted), functional equivalents of the CLP or mutants of the CLP. Such host animals may include but are not limited to rabbits, mice, goats, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Polyclonal antibodies are heterogeneous populations of antibody molecules derived from the sera of the immunized animals.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against CLP products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include, but are not limited to: the F(ab')$_2$ fragments which can be produced by pepsin digestion of the antibody molecule and the Fab fragments which can be generated by reducing the disulfide bridges of the F(ab' )$_2$ fragments. Alternatively, Fab expression libraries may be constructed (Huse et al., 1989, Science, 246:1275–1281) to allow rapid and easy identification of monoclonal Fab fragments with the desired specificity.

Antibodies to a CLP can, in turn, be utilized to generate anti-idiotype antibodies that "mimic" a given CLP, using techniques well known to those skilled in the art. (See, e.g., Greenspan & Bona, 1993, FASEB J 7(5):437–444; and Nissinoff, 1991, J. Immunol. 147(8):2429–2438). For example antibodies which bind to a CLP domain and competitively inhibit the binding of CLP to its cognate receptor can be used to generate anti-idiotypes that "mimic" the CLP and, therefore, bind and activate or neutralize a receptor. Such anti-idiotypic antibodies or Fab fragments of such anti-idiotypes can be used in therapeutic regimens involving the CLP regulatory or signaling pathways.

5.4 Diagnosis of Abnormalities Related to a CLP

A variety of methods can be employed for the diagnostic and prognostic evaluation of disorders related to CLP function, and for the identification of subjects having a predisposition to such disorders.

Such methods may, for example, utilize reagents such as the CLP nucleotide sequences described in Section 5.1, and CLP antibodies, as described, in Section 5.3. Specifically, such reagents may be used, for example, for: (1) the detection of the presence of CLP gene mutations, or the detection of either over- or under-expression of CLP mRNA relative to a given phenotype; (2) the detection of either an over- or an under-abundance of CLP gene product relative to a given phenotype; and (3) the detection of perturbations or abnormalities in any potential regulatory, signal transduction, metabolic, or catabolic pathway mediated by a CLP.

The methods described herein may be performed, for example, by utilizing pre-packaged diagnostic kits comprising at least one specific CLP nucleotide, or oligonucleotide, sequence or CLP antibody reagent described herein, which may be conveniently used, e.g., in clinical settings, to diagnose patients exhibiting body weight, or other physiological, mental or chemical disorders, dysfunctions, or abnormalities.

For the detection of CLP mutations, any nucleated cell can be used as a starting source for genomic nucleic acid. For the detection of CLP gene expression or CLP products, any cell type or tissue in which the CLP gene is expressed, such as, for example, brain or testis cells, may be utilized.

Nucleic acid-based detection techniques are described, below, in Section 5.4.1. Peptide detection techniques are described, below, in Section 5.4.2.

5.4.1 Detection of CLP Genes and Transcripts

Mutations within a CLP, and particularly HCLP, gene can be detected by utilizing a number of techniques. Nucleic acid from any nucleated cell can be used as the starting point for such assay techniques, and may be isolated according to standard nucleic acid preparation procedures which are well known to those of skill in the art.

DNA may be used in hybridization or amplification assays of biological samples to detect abnormalities involving CLP gene structure, including point mutations, insertions, deletions and chromosomal rearrangements. Such assays may include, but are not limited to, Southern analyses, single stranded conformational polymorphism analyses (SSCP), and PCR analyses.

Such diagnostic methods for the detection of CLP gene-specific mutations can involve, for example, contacting and incubating nucleic acids including recombinant DNA molecules, cloned genes or degenerate variants thereof, obtained from a sample, e.g., derived from a patient sample or other appropriate cellular source, with one or more labeled nucleic acid reagents including recombinant DNA molecules, cloned genes or degenerate variants thereof, as described in Section 5.1, under conditions favorable for the specific annealing of these reagents to their complementary sequences within a given CLP gene. Preferably, the lengths of these nucleic acid reagents are at least 15 to 30 nucleotides. After incubation, all non-annealed nucleic acids are removed from the nucleic acid:CLP molecule hybrid. The presence of nucleic acids which have hybridized, if any such molecules exist, is then detected. Using such a detection scheme, the nucleic acid from the cell type or tissue of interest can be immobilized, for example, to a solid support such as a membrane, or a plastic surface such as that on a microtiter plate or polystyrene beads. In this case, after incubation, non-annealed, labeled nucleic acid reagents of the type described in Section 5.1 are easily removed. Detection of the remaining, annealed, labeled CLP nucleic acid reagents is accomplished using standard techniques well-known to those in the art. The CLP gene sequences to which the nucleic acid reagents have annealed can be compared to the annealing pattern expected from a normal CLP gene sequence in order to determine whether a CLP gene mutation is present.

Alternative diagnostic methods for the detection of CLP gene specific nucleic acid molecules, in patient samples or other appropriate cell sources, may involve their amplification, e.g., by PCR (the experimental embodiment set forth in Mullis, K. B., 1987, U.S. Pat. No. 4,683,202), followed by the detection of the amplified molecules using techniques well known to those of skill in the art. The resulting. amplified sequences can be compared to those which would be expected if the nucleic acid being amplified contained only normal copies of a CLP gene in order to determine whether a CLP gene mutation exists.

Additionally, well-known genotyping techniques can be performed to identify individuals carrying CLP gene mutations. Such techniques include, for example, the use of restriction fragment length polymorphisms (RFLPs), which involve sequence variations in one of the recognition sites for the specific restriction enzyme used.

Additionally, improved methods for analyzing DNA polymorphisms which can be utilized for the identification of CLP gene mutations have been described which capitalize on the presence of variable numbers of short, tandemly repeated DNA sequences between the restriction enzyme sites. For example, Weber (U.S. Pat. No. 5,075,217, which is incorporated herein by reference in its entirety) describes a DNA marker based on length polymorphisms in blocks of (dC-dA)n-(dG-dT)n short tandem repeats. The average separation of (dC-dA)n-(dG-dT)n blocks is estimated to be 30,000–60,000 bp. Markers which are so closely spaced exhibit a high frequency co-inheritance, and are extremely useful in the identification of genetic mutations, such as, for example, mutations within a given CLP gene, and the diagnosis of diseases and disorders related to CLP mutations.

Also, Caskey et al. (U.S. Pat. No. 5,364,759, which is incorporated herein by reference in its entirety) describe a DNA profiling assay for detecting short tri and tetra nucleotide repeat sequences. The process includes extracting the DNA of interest, such as the CLP gene, amplifying the extracted DNA, and labeling the repeat sequences to form a genotypic map of the individual's DNA.

The level of CLP gene expression can also be assayed by detecting and measuring CLP transcription. For example, RNA from a cell type or tissue known, or suspected to express the CLP gene, such as brain, may be isolated and tested utilizing hybridization or PCR techniques such as are described, above. The isolated cells can be derived from cell culture or from a patient. The analysis of cells taken from culture may be a necessary step in the assessment of cells to be used as part of a cell-based gene therapy technique or, alternatively, to test the effect of compounds on the expression of the CLP gene. Such analyses may reveal both quantitative and qualitative aspects of the expression pattern of the CLP gene, including activation or inactivation of CLP gene expression.

In one embodiment of such a detection scheme, cDNAs are synthesized from the RNAs of interest (e.g., by reverse transcription of the RNA molecule into cDNA). A sequence within the cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from among the CLP nucleic acid reagents described in Section 5.1. The preferred lengths of such nucleic acid reagents are at least about 9–30 nucleotides. For detection of the amplified product, the nucleic acid amplification may be performed using radioactively or non-radioactively labeled nucleotides. Alternatively, enough amplified product may be made such that the product may be visualized by standard ethidium bromide staining, by utilizing any other suitable nucleic acid staining method, or by sequencing.

Additionally, it is possible to perform such CLP gene expression assays "in situ", i.e., directly upon tissue sections (fixed and/or frozen) of patient tissue obtained from biopsies or resections, such that no nucleic acid purification is necessary. Nucleic acid reagents such as those described in Section 5.1 may be used as probes and/or primers for such in situ procedures (See, for example, Nuovo, G. J., 1992, "PCR In Situ Hybridization: Protocols And Applications", Raven Press, N.Y.).

Alternatively, if a sufficient quantity of the appropriate cells can be obtained, standard Northern analysis can be performed to determine the level of mRNA expression of the CLP gene.

5.4.2 Detection of CLP Products

Antibodies directed against wild type or mutant CLP products or conserved variants or peptide fragments thereof, which are discussed above in Section 5.3, may also be used as diagnostics and prognostics, as described herein. Such diagnostic methods, may be used to detect abnormalities in the level of CLP gene expression, or abnormalities in the structure and/or temporal, tissue, cellular, or subcellular location of the CLP, and may be performed in vivo or in vitro, such as, for example, on biopsy tissue.

For example, antibodies directed to epitopes of a CLP can be used in vivo to detect the pattern and level of expression of the CLP in the body. Such antibodies can be labeled, e.g., with a radio-opaque or other appropriate compound and injected into a subject in order to visualize binding to the CLP expressed in the body using methods such as X-rays, CAT-scans, or MRI. Labeled antibody fragments, e.g., the Fab or single chain antibody comprising the smallest portion of the antigen binding region, are preferred for this purpose to promote crossing the blood-brain barrier and permit labeling of CLPs expressed in the brain.

Additionally, any CLP-fusion protein or CLP-conjugated protein whose presence can be detected, can be administered. For example, CLP-fusion or conjugated proteins labeled with a radio-opaque or other appropriate compound can be administered and visualized in vivo, as discussed, above for labeled antibodies. Further such CLP fusion proteins (such as AP-CLP or CLP-AP) can be utilized for in vi tro diagnostic procedures.

Alternatively, immunoassays or fusion protein detection assays, as described above, can be utilized on biopsy and autopsy samples in vitro to permit assessment of the expression pattern of the CLP. Such assays are not confined to the use of antibodies that define a CLP domain, but can include the use of antibodies directed to epitopes of any domain of a CLP. The use of each or all of these labeled antibodies will yield useful information regarding translation and intracellular transport of the CLP to the cell surface and can identify defects in processing.

The tissue or cell type to be analyzed will generally include those which are known, or suspected, to express the CLP gene, such as, for example, epithelial cells, brain cells, etc. The protein isolation methods employed herein may, for example, be such as those described in Harlow and Lane (Harlow, E. and Lane, D., 1988, "Antibodies: A Laboratory Manual", Cold Spring Harbor Laboratory Press, Cold Spring Harbor, N.Y.), which is incorporated herein by reference in its entirety. The isolated cells can be derived from cell culture or from a patient. The analysis of cells taken from culture may be a necessary step in the assessment of cells that could be used as part of a cell-based gene therapy technique or, alternatively, to test the effect of compounds on the expression of a CLP gene.

For example, antibodies, or fragments of antibodies, such as those described, above, in Section 5.3, useful in the present invention may be used to quantitatively or qualitatively detect the presence of CLP products or conserved variants or peptide fragments thereof. This can be accomplished, for example, by immunofluorescence techniques employing a fluorescently labeled antibody (see below, this Section) coupled with light microscopic, flow cytometric, or fluorimetric detection. Such techniques are especially preferred if such CLP products are at least transiently present on the cell surface.

The antibodies (or fragments thereof) or CLP fusion or conjugated proteins useful in the present invention may, additionally, be employed histologically, as in immunofluorescence, immunoelectron microscopy or non-immuno assays, for in situ detection of CLP gene products or conserved variants or peptide fragments thereof, or to assay CLP binding (in the case of labeled CLP-fusion protein).

In situ detection may be accomplished by removing a histological specimen from a patient, and applying thereto a labeled antibody or fusion protein of the present invention. The antibody (or fragment) or fusion protein is preferably applied by overlaying the labeled antibody (or fragment) onto a biological sample. Through the use of such a procedure, it is possible to determine not only the presence of a CLP product, or conserved variants or peptide fragments, or CLP binding, but also its distribution in the examined tissue. Using the present invention, those of ordinary skill will readily perceive that any of a wide variety of histological methods (such as staining procedures) can be modified in order to achieve such in situ detection.

Immunoassays and non-immunoassays for CLP products, or conserved variants or peptide fragments thereof, will typically comprise incubating a sample, such as a biological fluid, a tissue extract, freshly harvested cells, or lysates of cells which have been incubated in cell culture, in the presence of a detectably labeled antibody capable of identifying CLP products or conserved variants or peptide fragments thereof, and detecting the bound antibody by any of a number of techniques well-known in the art. Alternatively, the labeled antibody can be directed against an antigenic tag that has been directly or indirectly attached to a CLP.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with a detectably labeled CLP antibody or CLP fusion protein. The solid phase support may then be washed with the buffer a second time to remove unbound antibody or fusion protein. The amount of bound label on the solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural. configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of CLP antibody or CLP ligand fusion protein may be determined according to well known methods. Those skilled in the art will be able to determine operative and optimal assay conditions for each determination by employing routine experimentation.

With respect to antibodies, one of the ways in which a CLP antibody can be detectably labeled is by linking the same to an enzyme and use in an enzyme immunoassay (EIA) (Voller, A., "The Enzyme Linked Immunosorbent Assay (ELISA)", 1978, Diagnostic Horizons 2:1–7, Microbiological Associates Quarterly Publication, Walkersville, Md.); Voller, A. et al., 1978, J. Clin. Pathol. 31:507–520; Butler, J. E., 1981, Meth. Enzymol. 73:482–523; Maggio, E. (ed.), 1980, Enzyme Immunoassay, CRC Press, Boca Raton, Fla.; Ishikawa, E. et al., (eds.), 1981, Enzyme Immunoassay, Kgaku Shoin, Tokyo). The enzyme that is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by calorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect CLP through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims. All references, citations, patents, and patent applications (international, provisional, and otherwise) cited herein are incorporated by reference in their entirety.

What is claimed is:

1. An isolated nucleic acid molecule, comprising a nucleotide sequence of SEQ ID NO:1.

2. An isolated nucleic acid molecule comprising a nucleotide sequence that encodes the amino acid sequence shown in SEQ ID NO:2.

3. A genetically engineered expression vector that comprises a nucleic acid molecule according to claim 2 operatively linked to a promoter element.

4. An isolated nucleic acid molecule comprising a nucleotide sequence that encodes the amino acid sequence shown in SEQ ID NO:4.

5. An isolated genetically engineered expression vector comprising a nucleic acid molecule according to claim 4 operatively linked to a promoter element.

6. An isolated preparation of cortexin-like protein comprising an amino acid sequence of SEQ ID NO:4.

* * * * *